(12) United States Patent
Chung et al.

(10) Patent No.: US 9,150,835 B2
(45) Date of Patent: Oct. 6, 2015

(54) MODIFIED MICROORGANISM FOR HIGHLY EFFICIENT PRODUCTION OF LACTIC ACID

(75) Inventors: Soon Chun Chung, Seoul (KR); Hyun Min Koo, Seoul (KR); Jae Young Kim, Suwon-si (KR); Ji Eun Kim, Seoul (KR); Jin Woo Kim, Seoul (KR); Young kyoung Park, Yongin-si (KR); So Young Lee, Daejeon (KR); Hwa Young Cho, Hwaseong-si (KR); Dae Huck Kweon, Suwon-si (KR); Jae Chan Park, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 232 days.

(21) Appl. No.: 13/531,356

(22) Filed: Jun. 22, 2012

(65) Prior Publication Data
US 2013/0065284 A1 Mar. 14, 2013

(30) Foreign Application Priority Data

Jun. 24, 2011 (KR) .................. 10-2011-0061695
Jun. 8, 2012 (KR) .................. 10-2012-0061819

(51) Int. Cl.
*C12N 15/81* (2006.01)
*C12P 7/56* (2006.01)
*C12N 15/63* (2006.01)
*C12N 9/04* (2006.01)

(52) U.S. Cl.
CPC ............ *C12N 9/0006* (2013.01); *C12N 15/815* (2013.01); *C12P 7/56* (2013.01); *C12N 15/81* (2013.01); *C12Y 101/01027* (2013.01)

(58) Field of Classification Search
CPC ........ C12P 7/57; C12N 15/815; C12N 9/0006
USPC ......... 435/135, 252.2, 252.3, 252.31, 252.33, 435/254.11, 320.1
See application file for complete search history.

(56) References Cited

U.S. PATENT DOCUMENTS

| 6,268,189 B1 | 7/2001 | Skory |
| 7,109,010 B2 | 9/2006 | Rajgarhia et al. |
| 7,132,522 B1 | 11/2006 | Becher et al. |

FOREIGN PATENT DOCUMENTS

| EP | 2221373 A1 | 8/2010 |
| EP | 2281881 A1 | 2/2011 |
| JP | 2008029329 A | 2/2008 |
| WO | WO 2004/065552 A2 | 8/2004 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Database UniProt [Online] Oct. 1, 2003, "SubName: Full=Upsilon-crystallin;", XP002688328, retrieved from EBI accession No. TR:Q7YQK6 Database accession No. Q7YQK6.
Database UniProt [Online] Sep. 22, 2009, "SubName: Full=M(A)-type lactate dehydrogenase; EC=1.1.1.27;", XP002688329, retrieved from EBI accession No. TR:C6L2F0 Database accession No. C6L2F0.
Database Geneseq [Online] Oct. 21, 2004, "Rat lactate dehydrogenase A.", XP002688330, retrieved from EBI accession No. GSP:ADQ94415 Database accession No. ADQ94415.
Echigoya et al., "Molecular characterization and expression pattern of the equine lactate dehydrogenase A and B genes," *Gene*, 447(1), 40-50 (Nov. 1, 2009).
Liao et al., Lactate dehydrogenase genes of caiman and Chinese soft-shelled turtle, with emphasis on the molecular phylogenetics and evolution of reptiles, *Gene*, 279(1), 63-67 (Nov. 14, 2001), abstract only.
Pecota et al., "Sequential gene integration for the engineering of *Kluyveromyces marxianus*," *J. of Biotech.*, 127(3), 408-416 (Dec. 1, 2006), abstract only.
Van Rheede et al., "Lactate Dehydrogenase A as a Highly Abundant Eye Lens Protein in Platypus (*Ornithorhynchus anatinus*): Upsilon (upsilon)-Crystallin," *Mol. Biol. and Evol.*, 20(6), 994-998 (Jun. 1, 2003), abstract only.
Nonklang et al., "High-Temperature Ethanol Fermentation and Transformation with Linear DNA in the Thermotolerant Yeast *Kluyveromyces marxianus* DMKU3-1042," *Applied and Environmental Microbiology*, 2008, 7514-7521, 74-24, American Society for Microbiology. (Abstract only).
Ball et al., "Construction of Efficient Centrometric, Multicopy and Expression Vectors for the Yeast *Kluyveromyces marxianus* Using Homologous Elements and the Promoter of a Purine-Cytosine-Like Permease," *J. Mol. Microbiol. Biotechnol*, 1999, 347-353, 1-2, Horizon Scientific Press.
Ishida et al., Efficient Production of $^L$-Lactic Acid by Metabolically Engineered *Saccharomyces cerevisiae* with a Genome-Integrated $^L$-Lactate Dehydrogenase Gene, *Applied and Environmental Microbiology*, 71 (4): 1964-1970 (2005).
European Patent Office, Examination Report in European Patent Application No. 12173385.1, Dec. 12, 2014, 6 pp.

* cited by examiner

*Primary Examiner* — Tekchand Saidha
*Assistant Examiner* — Md. Younus Meah
(74) *Attorney, Agent, or Firm* — Leydig, Voit & Mayer, Ltd.

(57) ABSTRACT

A modified microorganism for high efficient production of lactic acid, an expression vector for constructing the modified microorganism, and a method of producing a lactic acid using the same are disclosed. The modified microorganism may produce lactic acid at a high level under acid conditions.

22 Claims, 1 Drawing Sheet

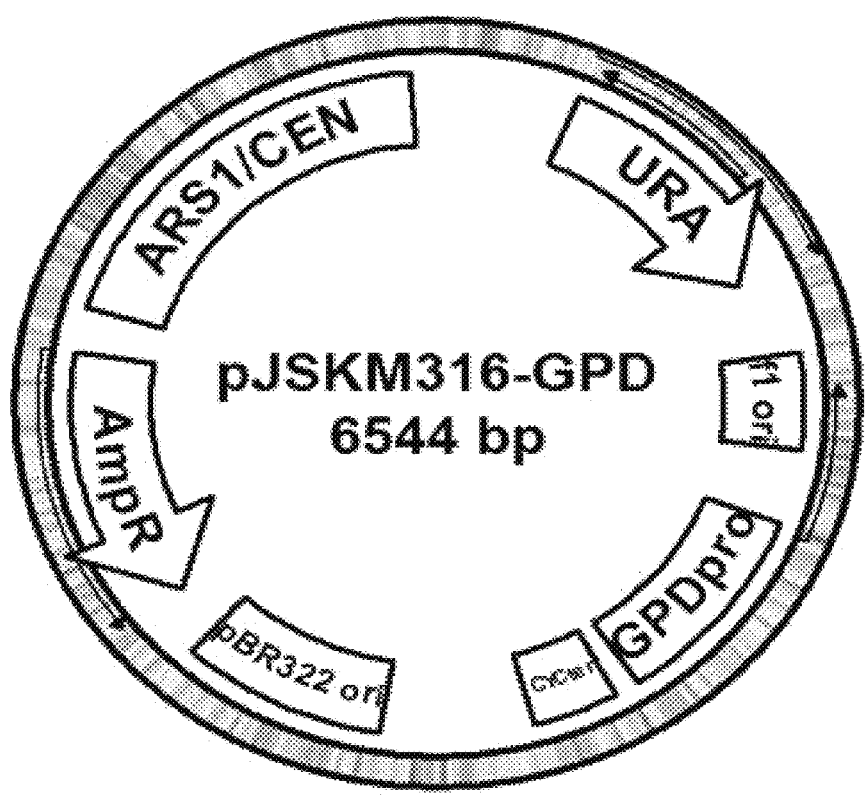

MODIFIED MICROORGANISM FOR HIGHLY EFFICIENT PRODUCTION OF LACTIC ACID

CROSS-REFERENCE TO RELATED APPLICATION

This application claims priority to Korean Patent Application No. 10-2011-0139520, filed on Dec. 21, 2011, Korean Patent Application No. 10-2011-0061695, filed on Jun. 24, 2011, and Korean Patent Application No. 10-2012-0061819, filed on Jun. 8, 2012, which are herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 588 Byte ASCII (Text) file named "710589ST25.txt," created on Jun. 21, 2012.

BACKGROUND

1. Field

Provided are a modified microorganism for high efficient production of lactic acid, an expression vector for constructing the modified microorganism, and a method of producing a lactic acid using the same.

2. Description of the Related Art

Lactic acid is an organic acid that plays a role in various industry such as cosmetics, chemical, metal, electronic, textile, dyeing and pharmaceutical industry as well as in various food additives such as preservatives, flavoring agents and acidulents. Further, lactic acid is used also as a monomer for producing polylactic acid ("PLA"), which is a biodegradable plastic. Recently, this kind of plastic is a good option for substituting conventional plastic produced from petroleum oil because of low emission of carbon dioxide.

Specifically, lactic acid has a hydroxyl group and a carboxyl group, making it greatly reactive such that it plays a important role as a source material on producing chemical including acetaldehyde, polypropylene glycol, acrylic acid, 2,3-pentathione as well as polylactic acid. Lactic acid is also used for producing ethyl lactate, which is a biodegradable and non-toxic solvent and used in electronic manufactures, paint or textile industry, detergents or printing industry.

Recently, strains of *Kluyveromyces* are being considered as viable alternatives to *Saccharomyces cerevisiae*. *Kluyveromyces marxianus* and *Kluyveromyces lactis* are classified as GRAS ("Generally Recognized As Safe") microorganisms, and may therefore be used with the same security as *Saccharomyces cerevisiae*.

*K. marxianus* is reported to grow at a temperature of 47° C., 49° C., and even 52° C., and shows superior acid resistance. Therefore, attention has been paid to *K. marxianus* as an organic acid- and platform compound-producing strain.

SUMMARY

According to an aspect of the invention, a modified microorganism for highly efficient production of lactic acid is provided, which expresses at least one lactate dehydrogenase ("LDH") enzyme of *Pelodiscus sinensis japonicus, Ornithorhynchus anatinus, Tursiops truncatus* or *Rattus norvegicus*.

According to another aspect of the invention, an expression vector comprising a replication origin, a promoter, a polynucleotide encoding at least one LDH enzyme of *Pelodiscus sinensis japonicus, Ornithorhynchus anatinus, Tursiops truncatus* or *Rattus norvegicus*, and a terminator is disclosed.

According to another aspect of the invention, a method of producing a lactic acid comprising culturing the modified microorganism including above expression vector in a glucose-containing medium to produce lactic acid, and recovering the lactic acid from the medium is disclosed.

The modified microorganism may produce lactic acid at a high level, even under acidic conditions.

BRIEF DESCRIPTION OF THE DRAWINGS

FIG. 1 is a diagram depicting an pJSKM316-GPD according to Example 1.

DETAILED DESCRIPTION

Unless otherwise indicated, the practice of the disclosure involves conventional techniques commonly used in molecular biology, microbiology, protein purification, protein engineering, protein and DNA sequencing, and recombinant DNA fields, which are within the skill of the art. Such techniques are known to those of skill in the art, and are described in numerous standard texts and reference works. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxyl orientation, respectively.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the specification as a whole.

A modified microorganism for high efficient production of lactic acid is provided herein. Certain organic acids such as lactic acid are manufactured through an industrial fermentation process. The fermentation is conducted using various types of bacterial species, which consume sugars and convert those sugars to the desired acid.

There are several reasons why it would be desirable to develop a yeast or fungal biocatalyst for producing organic acids from sugar substrates. Many bacteria are unable to synthesize some of the amino acids or proteins they need to grow and metabolize sugars efficiently. As a result, bacteria often must be fed a somewhat complex package of nutrients. This increases the direct expense required to operate the fermentation. The increased complexity of the broth makes it more difficult to recover the fermentation product in reasonably pure form, so increased operating and capital costs are incurred to recover the product. On the other hand, many yeast species can synthesize their needed amino acids or proteins from inorganic nitrogen compounds. They often grow and ferment well in so-called "defined" media, which are simplified, often less expensive and present fewer difficulties in product recovery operations.

Another reason that yeast are of interest as a biocatalyst for organic acid production has to do with the nature of the product itself. To have an economically viable process, a high concentration of the organic acid product must accumulate in the fermentation broth. In addition to the normal concerns about toxicity (the fermentation product may be toxic to the biocatalyst when present in high concentrations), an additional concern about acidity exists when the fermentation product is an acid. The media will become increasingly acidic as more of the organic acid is produced. Most bacteria that produce these organic acids do not perform well in strongly acidic environments, they either do not survive under those conditions or else produce the product so slowly as to be economically unviable.

For this reason, commercial acid fermentation processes are buffered by the addition of an agent which neutralizes the acid as it formed. This maintains the broth at or near a neutral pH and allows the bacteria to grow and produce efficiently. However, this converts the acid to a salt, which subsequently must be split to obtain the product in its desired acid form.

The most common buffering agent is a calcium compound, which neutralizes the organic acid to form the corresponding calcium salt. After the calcium salt is recovered from the fermentation broth, it is split by the addition of a mineral acid, typically sulfuric acid, to regenerate the organic acid and form an insoluble calcium salt of the mineral acid. This process therefore involves direct expense for the buffering agent and mineral acid, as well as costs for handling and disposing the unwanted calcium salt by-product. These costs may be reduced or eliminated if the biocatalyst could grow and produce efficiently under lower pH conditions.

According to one embodiment, a modified microorganism comprising a heterologous activity of a lactate dehydrogenase ("LDH") is provided.

As used herein, the term "metabolically engineered" or "metabolic engineering" involves rational pathway design and assembly of biosynthetic genes, genes associated with operons, and control elements of such nucleic acid sequences, for the production of a desired metabolite, such as an alcohol, in a microorganism. "Metabolically engineered" can further include optimization of metabolic flux by regulation and optimization of transcription, translation, protein stability and protein functionality using genetic engineering and appropriate culture condition. The biosynthetic genes can be heterologous to the host (e.g., microorganism), either by virtue of being foreign to the host, or being modified by mutagenesis, recombination, or association with a heterologous expression control sequence in an endogenous host cell. Appropriate culture conditions are conditions such as culture medium pH, ionic strength, nutritive content, etc., temperature, oxygen, $CO_2$, nitrogen content, humidity, and other culture conditions that permit production of the compound by the host microorganism, i.e., by the metabolic action of the microorganism. Appropriate culture conditions are well known for microorganisms that can serve as host cells.

Accordingly, a metabolically "engineered" or "modified" microorganism is produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite.

For example, the introduction of genetic material into a parental microorganism results in a new or modified ability to produce a chemical. The genetic material introduced into the parental microorganism contains gene, or parts of genes, coding for one or more of the enzymes involved in a biosynthetic pathway for the production of a chemical and may also include additional elements for the expression or regulation of expression of these genes, e.g. promoter sequences.

As used herein, the term "exogenous" or "heterologous" means that a biological function or material, including genetic material, of interest is not natural in a host strain. The term "native" means that such biological material or function naturally exists in the host strain or is found in a genome of a wild-type cell in the host strain.

As used interchangeably herein, the terms "activity" and "enzymatic activity" refer to any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof.

As used herein, the term "lactate dehydrogenase (LDH)" refers to an enzyme that has the ability to convert pyruvate into lactate. LDH enzymes are divided into four classes: cytochrome C-dependent D- and L-lactate dehydrogenases (EC 1.1.2.4 and EC 1.1.2.3) and NAD(P)-dependent D- and L-lactate dehydrogenases (EC 1.1.1.28 and EC 1.1.1.27). The embodiment is related to NAD(P)-dependent L-lactate dehydrogenase.

As used herein, the term "derived from" means that a genetic material is wholly or partially isolated or purified from a given source.

The pyruvate to lactate conversion by LDH is represented by the following Scheme 1:

Scheme 1

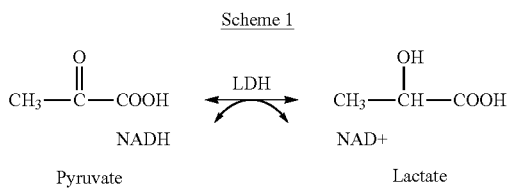

Pyruvate                                Lactate

In the embodiment, the LDH activity may include an LDH activity derived from a source of a bacterium, fungus, yeast, mammal or reptile. According to the exemplary embodiment, LDH genes coding for enzymes having a high-efficiency LDH activity are screened through a database search. For example, L-LDH genes are listed from the database, and representative genes are selected from the L-LDH genes using enzyme homology and phylogenetic analysis. In an exemplary embodiment, the LDH activities derived from *Pelodiscus sinensis japonicus, Ornithorhynchus anatinus, Tursiops truncatus* and *Rattus norvegicus* are used.

The LDH activity may be introduced to a microorganism by a known method in the art. For example, the method may include manufacturing a expression vector including a gene having the activities, and then transforming a microorganism with the expression vector.

In another embodiment, an expression vector for constructing the modified microorganism is provided. The expression vector may comprise a replication origin; a promoter; a polynucleotide encoding a LDH activity; and a terminator.

As used herein, the term "replication origin" refers to a nucleotide sequence at which replication or amplification of a plasmid begins in a host cell.

As used herein, the term "expression vector" refers to a DNA construct containing a DNA sequence that is operably linked to a suitable control sequence capable of effecting the expression of the DNA in a suitable host. The vector may be a plasmid, a phage particle, or simply a potential genomic insert. Once transformed into a suitable host, the vector replicates and functions independently of the host genome, or integrates into the genome itself. As used herein, the terms "plasmid," "expression plasmid," and "vector" are often used interchangeably as a plasmid is among the most commonly used forms of vector at present.

However, it is intended to include such other forms of expression vectors that serve equivalent functions and which are, or become, known in the art. For example, the vector may be a cloning vector, an expression vector, a shuttle vector, a plasmid, a phage or virus particle, a DNA construct, or a cassette. As used herein, the term "plasmid" refers to a circular double-stranded DNA construct used as a cloning vector, and which forms an extra chromosomal self-replicating genetic element in many bacteria and some eukaryotes. The plasmid may be a multicopy plasmid that can integrate into the genome of the host cell by homologous recombination.

As known to those skilled in the art, to increase the expression level of a gene introduced to a host cell, the gene should be operably linked to expression control sequences for the control of transcription and translation which function in the selected expression host. For example, the expression control sequences and the gene are included in one expression vector together with a selection marker and a replication origin. When the expression host is a eukaryotic cell, the expression vector should further include an expression marker useful in the eukaryotic expression host.

As used herein, the term "operably linked" indicates that elements are arranged to perform the general functions of the elements. A nucleic acid is said to be "operably linked" when it is placed into a functional relationship with another nucleic acid sequence. For example, a polynucleotide promoter sequence is operably linked to a polynucleotide encoding a polypeptide if it affects the transcription of the sequence. The term "operably linked" may mean that the polynucleotide sequences being linked are contiguous Linking may be accomplished by ligation at convenient restriction sites. If such sites do not exist, synthetic oligonucleotide adaptors or linkers may be used in accordance with conventional practice.

As used herein, the term "promoter" refers to a nucleic acid sequence that functions to drive or effect transcription of a downstream gene. In an embodiment, the promoter is functional in *Kluyveromyces*. In some embodiments, the promoter may be any promoter that drives expression of lactate dehydrogenase. A promoter may be any nucleic acid sequence which shows transcriptional activity in the host cell of choice and includes mutant, truncated and hybrid promoters, and may be obtained from genes encoding extracellular or intracellular polypeptides either homologous or heterologous to the host cell. The promoter sequence may be native or foreign to the host cell.

As used herein, the term "gene" refers to a chromosomal segment of DNA involved in producing a polypeptide chain that may or may not include regions preceding and following the coding regions, for example, 5' untranslated ("5' UTR") or leader sequences and 3' untranslated ("3' UTR") or trailer sequences, as well as intervening sequence (introns) between individual coding segments (exons).

As used interchangeably herein, the terms "polynucleotide" and "nucleic acid" refer to a polymeric form of nucleotides of any length. These terms include, but are not limited to, a single-stranded DNA ("deoxyribonucleic acid"), double-stranded DNA, genomic DNA, cDNA, or a polymer comprising purine and pyrimidine bases, or other natural, chemically-modified, biochemically-modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA ("ribonucleic acid") of any sequence, nucleic acid probes, and primers. It will be understood that, as a result of the degeneracy of the genetic code, a multitude of nucleotide sequences encoding a given protein may be produced.

As used herein, the term "terminator" refers to a nucleic acid sequence that functions to drive or effect termination of transcription.

In some embodiments, the replication origin may include an autonomous replication sequence ("ARS"), and the ARS may be stabilized by a centromeric sequence ("CEN"). In an exemplary embodiment, ARS/CEN from *K. marxianus* is used.

The ARS/CEN replication origin may include SEQ ID NO: 1, or at least about 70%, at least about 75%, at least about 80%, at least about 85%, at least about 90%, at least about 92%, at least about 95%, at least about 97%, at least about 98% or at least about 99% sequence homology to the SEQ ID NO: 1.

In some embodiments, the promoter may be, but is not limited to, CYC ("cytochrome-c oxidase"), TEF ("translation elongation factor 1α"), GPD ("glyceraldehyde-3-phosphate dehydrogenase"), ADH ("alcohol dehydrogenase"), PHO5, TRP1, GAL1, GAL10, hexokinase, pyruvate decarboxylase, phosphofructokinase, triose phosphate isomerase, phosphoglucose isomerase, glucokinase, α-mating factor pheromone, GUT2, nmt, fbp1, AOX1, AOX2, MOX1, FMD1 and PGK1. Particularly, the promotor may be selected from the group consisting of CYC, TEF, GPD and ADH. In an exemplary embodiment, GPD promoter is used.

The CYC promoter may include SEQ ID NO: 2, or at least about 70%, at least about 75%, at least about 80%, at least about 85%, at least about 90%, at least about 92%, at least about 95%, at least about 97%, at least about 98% or at least about 99% sequence homology to the SEQ ID NO: 2.

The TEF promoter may include SEQ ID NO: 3, or at least about 70%, at least about 75%, at least about 80%, at least about 85%, at least about 90%, at least about 92%, at least about 95%, at least about 97%, at least about 98% or at least about 99% sequence homology to the SEQ ID NO: 3.

The GPD promoter may include SEQ ID NO: 4, or at least about 70%, at least about 75%, at least about 80%, at least about 85%, at least about 90%, at least about 92%, at least about 95%, at least about 97%, at least about 98% or at least about 99% sequence homology to the SEQ ID NO: 4.

The ADH promoter may include SEQ ID NO: 5, or at least about 70%, at least about 75%, at least about 80%, at least about 85%, at least about 90%, at least about 92%, at least about 95%, at least about 97%, at least about 98% or at least about 99% sequence homology to the SEQ ID NO: 5.

The polynucleotide encoding the LDH activity may include SEQ ID NO: 6 (Accession Number: Q98SL0) derived from *Pelodiscus sinensis japonicus*, or at least about 70%, at least about 75%, at least about 80%, at least about 85%, at least about 90%, at least about 92%, at least about 95%, at least about 97%, at least about 98% or at least about 99% sequence homology to the SEQ ID NO: 6.

The polynucleotide encoding the LDH activity may include SEQ ID NO: 7 (Accession Number: Q7YQK6) derived from *Ornithorhynchus anatinus*, or at least about 70%, at least about 75%, at least about 80%, at least about 85%, at least about 90%, at least about 92%, at least about 95%, at least about 97%, at least about 98% or at least about 99% sequence homology to the SEQ ID NO: 7.

The polynucleotide encoding the LDH activity may include SEQ ID NO: 8 (Accession Number: C6L2F0) derived from *Tursiops truncatus*, or at least about 70%, at least about 75%, at least about 80%, at least about 85%, at least about 90%, at least about 92%, at least about 95%, at least about 97%, at least about 98% or at least about 99% sequence homology to the SEQ ID NO: 8.

The polynucleotide encoding the LDH activity may include SEQ ID NO: 9 (Accession Number: P04642) derived from *Rattus norvegicus*, or at least about 70%, at least about 75%, at least about 80%, at least about 85%, at least about 90%, at least about 92%, at least about 95%, at least about 97%, at least about 98% or at least about 99% sequence homology to the SEQ ID NO: 9.

In the embodiment, the terminator may be, but is not limited to, PGK1 (phosphoglycerate kinase 1), CYC1 (Cytochrome c transcription), and GAL1. In an exemplary embodiment, CYC1 terminator is used.

The CYC1 terminator may include SEQ ID NO: 10, or at least about 70%, at least about 75%, at least about 80%, at least about 85%, at least about 90%, at least about 92%, at least about 95%, at least about 97%, at least about 98% or at least about 99% sequence homology to the SEQ ID NO: 10.

As used herein, the term "homology" refers to sequence similarity or identity. This homology may be determined using standard techniques known in the art (See e.g., Smith and Waterman, Adv. Appl. Math., 2:482 [1981]; Needleman and Wunsch, J. MoI. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

The expression vector may further comprise a selectable marker. As used herein, the term "selectable marker" refers to a nucleotide sequence which is capable of expression in the host cells and where expression of the selectable marker confers to cells containing the expressed gene the ability to grow in the presence of a corresponding selective agent or in the absence of an essential nutrient. For example, the selectable marker may be, but is not limited to, resistance genes to antimicrobials such as kanamycin, erythromycin, actinomycin, chloramphenicol and tetracycline, or essential nutrient biosynthetic gene such as URA3, LEU2, TRP1 and HIS3. That is, selectable markers are genes that confer antimicrobial resistance or alter nutrient requiremnts of the host cell to allow cells containing the exogenous DNA to be distinguished from cells that have not received any exogenous sequence during the transformation. In an exemplary embodiment, URA3 is used as a selectable marker gene.

The expression vector may be introduced to a host cell by a known method in the art.

As used herein, the term "host cell" refers to a suitable cell that serves as a host for an expression vector. A suitable host cell may be a naturally occurring or wild-type host cell, or it may be an altered host cell. A "wild-type host cell" is a host cell that has not been genetically altered using recombinant methods.

As used herein, the term "altered host cell" refers to a genetically engineered host cell wherein a gene is expressed at an altered level of expression compared to the level of expression of the same gene in an unaltered or wild-type host cell grown under essentially the same growth conditions. In an embodiment, an altered host cell is one in which the gene is expressed or produced at a level of expression or production that is higher than the level of expression or production of gene in the unaltered or wild-type host cell grown under essentially the same growth conditions.

A "modified host cell" herein refer to a wild-type or altered host cell that has been genetically engineered to overproduce lactic acid. A modified host cell is capable of producing lactic acid at a greater level than its wild-type or altered parent host cell. The host cell may be selected from the group consisting of yeast and bacteria. For example, the genus of available host cells may be one selected from the group consisting of *Zymomonas, Escherichia, Pseudomonas, Alcaligenes, Salmonella, Shigella, Burkholderia, Oligotropha, Klebsiella, Pichia, Candida, Hansenula, Saccharomyces, Kluyveromyces, Comamonas, Corynebacterium, Brevibacterium, Rhodococcus, Azotobacter, Citrobacter, Enterobacter, Clostridium, Lactobacillus, Aspergillus, Zygosaccharomyces, Dunaliella, Debaryomyces, Mucor, Torulopsis, Methylobacteria, Bacillus, Rhizobium* and *Streptomyces*.

In the embodiment, the host cell may be, but is not limited to, a cell from the genus *Kluyveromyces* or the genus *Escherichia*. For example, the genus *Kluyveromyces* may be, but is not limited to, *K. marxianus, K. fragilis, K. lactis, K. bulgaricus*, and *K. thermotolerans*. In an exemplary embodiment, a *K. marxianus* cell and an *E. coli* cell are used.

As used herein, the term "introduced" refers to any method suitable for transferring the nucleic acid sequence into the cell. Such a method for introduction may be, but is not limited to, protoplast fusion, transfection, transformation, conjugation, and transduction (See e.g., Ferrari et al., "Genetics," in Hardwood et al., (eds.), *Bacillus*, Plenum Publishing Corp., pages 57-72, [1989]).

As used herein, the terms "transformed" and "stably transformed" refer to a cell that has a non-native heterologous polynucleotide sequence integrated into its genome or has the heterologous polynucleotide sequence present as an episomal plasmid that is maintained for at least two generations.

The introduction of the polynucleotide encoding the LDH activity to a host cell may be performed by isolating a plasmid from *E. coli* and then by transforming the plasmid into the host cell. However, it is not essential to use intervening microorganisms such as *E. coli*, a vector is directly introduced into a host cell. Transformation may be achieved by any one of various means including electroporation, microinjection, biolistics (or particle bombardment-mediated delivery), or *agrobacterium*-mediated transformation.

A method of producing lactic acid using the modified microorganism also is provided herein. The method may comprise culturing the modified microorganism in a glucose-containing medium so that the microorganism produces lactic acid, and recovering the lactic acid from the medium.

The method further includes producing lactide from the recovered lactic acid. Also, the method further includes polymerizing the lactide to prepare a polylactide polymer.

The step of culturing the modified microorganism may be performed under conditions suitable for the fermentation. The medium used to culture the cells comprises any conventional suitable medium known in the art for growing the host cells, such as minimal or complex media containing appropriate supplements. Suitable media are available from commercial suppliers or may be prepared according to published recipes (e.g., in catalogues of the American Type Culture Collection). In the exemplary embodiment, the medium may be a fermentation medium containing sugars that can be fermented by a genetically modified microorganism. The sugar may be a hexose, for example, glucose, glycan or another polymer of glucose, a glucose oligomer, for example, maltose, maltotriose or isomaltotriose, panose, fructose or a fructose oligomer. In addition, the fermentation medium may contain nitrogen sources such as ammonia, ammonium sulfate, ammonium chloride, ammonium nitrate and urea; inorganic salts such as potassium monohydrogen phosphate, potassium dihydrogen phosphate and magnesium sulfate; and optionally a nutrient including various vitamin such as peptone, a meat extract, a yeast extract, a corn steep liquor, casamino acid, biotin and thiamine.

The host cells may be cultured under batch, fed-batch, or continuous fermentation conditions. Classical batch fermentation methods use a closed system, in which the culture medium is made prior to the beginning of the fermentation run, the medium is inoculated with the desired organism, and fermentation occurs without subsequent addition of any components to the medium. In certain cases, the pH or oxygen content of the growth medium is altered during batch methods, but the content carbon source content is not altered. The metabolites and cell biomass of the batch system change constantly up to the time the fermentation is stopped. In a batch system, cell growth usually progresses through a static lag phase to a high growth log phase and finally to a stationary phase where the growth rate is diminished or halted. If untreated, cells in the stationary phase eventually die. In general, cells in log phase produce the most protein.

A variation on the standard batch ferementation is a "fed-batch fermentation" system. In fed-batch fermentation, nutrients (e.g., a carbon source, nitrogen source, O2, and typically, other nutrients) are only added when their concentration in culture falls below a threshold. Fed-batch systems are useful when catabolite repression is apt to inhibit the metabolism of the cells and where it is desirable to have limited amounts of nutrients in the medium. Actual nutrient concentration in fed-batch systems are estimated on the basis of the changes of measurable factors such as pH, dissolved oxygen and the partial pressure of waste gases such as $CO_2$. Batch and fed-batch fermentations are common and well known in the art.

Continuous fermentation is an open system in which a defined culture medium is added continuously to a bioreactor and an equal amount of conditioned medium is removed simultaneously for processing. Continuous fermentation generally maintains the cultures at a constant high density where cells are primarily in log phase growth. Continuous fermentation allows for the modulation of one factor or any number of factors that affect cell growth and/or end product concentration. For example, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art.

During the culturing, the medium may be buffered in a pH range of approximately 5.0 to approximately 9.0, or approximately 5.5 to approximately 7.0. A suitable buffer may be a basic substance that can neutralize a lactic acid when the lactic acid is formed, and may include, but is not limited to, potassium hydroxide, calcium carbonate, sodium hydroxide, potassium hydroxide, potassium carbonate, sodium carbonate, ammonium carbonate, ammonia and ammonium hydroxide.

The culturing may be performed so that a pH value of the medium can be equal to or less than a pKa value of lactic acid at the end of fermentation. For example, a final pH value may be in a range of approximately 1.5 to approximately 4.5, or approximately 2.0 to approximately 3.5, or approximately 2.5 to 3.0. The microorganism according to the exemplary embodiment may grow in an acidic fermentation medium having a pH value of less than approximately 3.5, less than approximately 3.3, and even less than approximately 3.1 to produce lactic acid.

The step of recovering the chemical from the medium may be performed any method. For example, the method may include salting-out, recrystallization, extraction with organic solvent, esterification distillation, chromatography, and electrodialysis, and the method for separation, purification, or collection may be appropriately selected according to the characteristics of the chemical.

According to the exemplary embodiment, the modified microorganism may produce a high yield of the lactic acid. For instance, the modified microorganism that expresses a heterologous LDH enzyme, as described herein, may produce a lactic acid yield that is greater than the lactic acid yield of same type of microorganism that has not been modified to express the heterologous LDH enzyme.

In an exemplary embodiment, the modified microorganism shows a yield of about 30% or more (e.g., about 34.50% or more or about 35% or more). Moreover, the modified microorganism shows a yield of about 10% or more (e.g., about 12% or 12.20% or more) even under the condition of approximately pH 3.0.

Hereinafter, the invention will be described in further detail with respect to exemplary embodiments. However, it should be understood that the invention is not limited to these Examples and may be embodied in various modifications and changes.

EXAMPLES

Strains and Plasmid

*E. coli* TOP10 F-mcrA Δ(mrr-hsdRMS-mcrBC) φ80lacZΔM15 ΔlacX74 nupG recA1 araD139 Δara-leu)7697 galE15 galK16 rpsL(StrR) endA1 λ-XL1 Blue(endA1 gyrA96(nalR) thi-1 recA1 relA1 lac glnV44 F'[::Tn10 proAB+lacIq Δ(lacZ)M15] hsdR17(rK-mK+)(Invitrogen, CA) is used for amplification of a plasmid. *Kluyveromyces marxianus* var. *marxianus*, for example KM07 (ATCC 36907) is used as a yeast host cell for production of lactic acid. The pRS306 (ATCC 77141) is used as a plasmid for recombination of a gene.

Medium and Method for Culturing

E. coli is inoculated in LB medium (1% bacto-trypton, 0.5% bacto-yeast extract, 1% NaCl) having ampicillin and kanamycin, and then cultured at a temperature of 37° C. A yeast host cell and a recombinant yeast are cultured in YPD medium(1% bacto-yeast extract, 2% bacto-pepton, 2% dextrose) at a temperature of 37° C. for 2 days. Minimal medium includes 0.17% yeast nitrogen base, 0.5% ammonium sulfate, 2% glucose or glycerol, 38.4 mg/l arginine, 57.6 mg/l isoleucine, 48 mg/l phenylalanine, 57.6% mg/l valine, 6 mg/l threonine, 50 mg/l inositol, 40 mg/l tryptophan, 15 mg/l tyrosine, 60 mg/l leusine and 4 mg/l histidine.

Example 1

Construction of Expression Vector for High Efficient Production of Lactic Acid

A. pKM316

The ARS/CEN replication origin from *K. marxianus* is amplified by means of a polymerase chain reaction (PCR) at an optimal annealing temperature ("TaOpt") of 53.2° C. using the following primers:

```
Forward(FW) primer:
5'-TTCAGACGTCGAGCTCCTTTCATTTCTGAT-3'

Backward(BW) primer:
5'-TTCAGACGTCATCGATTGAAGTTTTGTCCA-3'
```

Next, the replication origin is digested with the restriction enzyme AatII, and then ligated into the plasmid pRS306 (ATCC 77141), digested with the same restriction enzyme, to construct a *K. marxianus-E. coli* shuttle vector, which is referred to as pKM316.

B. pJSKM316-GPD

A GPD promoter from *S. cerevisiae* and a CYC terminator from *K. marxianus* are amplified by means of PCR at TaOpt of 57.5° C. using the following primers:

```
FW primer:  5'-TTCAGGTACCGGCCGCAAATTAAAGCCTTC-3'

BW primer:  5'-TTCAGCGGCCGCAGTTTATCATTATCAATACT-3'

FW primer:  5'-TTCAGGTACCTCATGTAATTAGTTATGTCAC-3'

BW primer:  5'-TTCAGCGGCCGCGGCCGCAAATTAAAGCCT-3'
```

Next, the promoter and the terminator are digested with restriction enzymes NotI and KpnI, and then ligated into pKM316 which is digested with the same restriction enzymes to construct pJSKM316-GPD. A graphical representation of pJSKM316-GPD is provided in FIG. 1.

C. pJSKM316-GPD LDH CYC

Nucleic acids encoding LDH derived from *Pelodiscus sinensis japonicus* (SEQ ID NO: 6), *Ornithorhynchus anatinus* (SEQ ID NO: 7), *Tursiops truncatus* (SEQ ID NO: 8) and *Rattus norvegicus* (SEQ ID NO: 9) are digested with restriction enzymes BamHI and EcoRI, and each was then introduced into a vector pJSKM316-GPD digested in the same manner to construct four pJSKM316-GPD LDH CYC vectors.

As a control, LDH derived from *Xenopus laevis* is introduced into a vector pJSKM316-GPD in the same manner as described above to construct a pJSKM316-GPD LDH CYC vector.

Example 2

Evaluation of Production Yield of Genetically Modified *K. marxianus*

Each of the expression vectors constructed in Example 1 is introduced into a *K. marxianus* strain. KM07 is transformed with each of the five expression vectors pJSKM316-GPD LDH CYC using electrophoresis, and a production yield of the lactic acid is measured at pH 5.5. The results are listed in the following Table 1.

TABLE 1

| Origin of LDH genes | Lactic acid productivity (g/L/h) | Yield (%) |
|---|---|---|
| Pelodiscus sinensis japonicus | 1.02 | 35.70 |
| Ornithorhynchus anatinus | 0.99 | 34.77 |
| Tursiops truncatus | 0.98 | 35.18 |
| Rattus norvegicus | 0.97 | 36.07 |
| Xenopus laevis | 0.76 | 26.28 |

As listed in Table 1, it is seen that the lactic acid productivity of the *K. marxianus* strain containing LDH derived from one of *Pelodiscus sinensis japonicus, Ornithorhynchus anatinus, Tursiops truncatus* and *Rattus norvegicus* showed a yield of 34.77% or more (0.959 g/L/h), but the lactic acid productivity of the *K. marxianus* strain containing LDH derived from *Xenopus laevis* showed a yield of 26.28% or less (0.76 g/L/h).

In order to determine the lactic acid productivity of *K. marxianus* according to the exemplary embodiment under the acidic conditions, a production yield of lactic acid is measured at pH 3. The results are listed in the following Table 2.

TABLE 2

| Origin of LDH genes | Lactic acid productivity (g/L/h) | Yield (%) |
|---|---|---|
| Pelodiscus sinensis japonicus | 0.34 | 19.20 |
| Ornithorhynchus anatinus | 0.30 | 17.10 |
| Tursiops truncatus | 0.24 | 15.20 |
| Rattus norvegicus | 0.22 | 12.20 |

As listed in Table 2, it is seen that the lactic acid productivity of the *K. marxianus* strain containing LDH derived from one of *Pelodiscus sinensis japonicus, Ornithorhynchus anatinus, Tursiops truncatus* and *Rattus norvegicus* showed a yield of 12.20% or more (0.22 g/L/h) under the strong acid condition of pH 3.

Therefore, the respective *K. marxianus* strains containing LDH derived of *Pelodiscus sinensis japonicus, Ornithorhynchus anatinus, Tursiops truncatus* and *Rattus norvegicus* as prepared in Examples are industrially available since they can produce a high yield of lactic acid under the acid conditions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified microorganism for production of lactic acid that expresses at least one heterologous lactate dehydrogenase ("LDH") enzyme with at least about 95% sequence identity to SEQ ID NO: 6.

2. The modified microorganism of claim 1, wherein the modified microorganism is selected from the group consisting of yeast and bacteria.

3. The modified microorganism of claim 2, wherein the modified microorganism is *Zymomonas, Escherichia, Pseudomonas, Alcaligenes, Salmonella, Shigella, Burkholderia, Oligotropha, Klebsiella, Pichia, Candida, Hansenula, Saccharomyces, Kluyveromyces, Comamonas, Corynebacterium, Brevibacterium, Rhodococcus, Azotobacter, Citrobacter, Enterobacter, Clostridium, Lactobacillus, Aspergillus, Zygosaccharomyces, Dunaliella, Debaryomyces, Mucor, Torulopsis, Methylobacteria, Bacillus, Rhizobium* or *Streptomyces*.

4. The modified microorganism of claim 3, wherein the modified microorganism is either *Escherichia coli* or *Kluyveromyces marxianus*.

5. The modified microorganism of claim 1, wherein the modified microorganism comprises at least one heterologous nucleic acid encoding at least one LDH enzyme comprises SEQ ID NO: 6.

6. The modified microorganism of claim 1, wherein the modified microorganism produces lactic acid at a yield of about 34% or more.

7. The modified microorganism of claim 1, wherein the modified microorganism produces lactic acid at a yield of about 12.20% or more at a pH of about 3.0.

8. An expression vector for constructing a modified microorganism of claim 1, comprising:
a replication origin;
a promoter;
a polynucleotide encoding at least one LDH enzyme with at least about 95% sequence identity to SEQ ID NO: 6; and
a terminator.

9. The expression vector of claim 8, wherein the replication origin is an autonomous replication sequence/centromeric sequence ("ARS/CEN").

10. The expression vector of claim 9, wherein the ARS/CEN replication origin comprises SEQ ID NO. 1 or a sequence with at least 70% sequence identity to the SEQ ID NO. 1.

11. The expression vector of claim 8, wherein the promoter is a CYC promoter, TEF promoter, GPD promoter, or ADH promoter.

12. The expression vector of claim 11, wherein the promoter is
(a) a CYC promoter comprising SEQ ID NO: 2 or a sequence with at least about 70% sequence identity to SEQ ID NO: 2;
(b) a TEF promoter comprising SEQ ID NO: 3 or a sequence with at least about 70% sequence identity to SEQ ID NO: 3
(c) a GDP promoter comprising SEQ ID NO: 4 or a sequence with at least about 70% sequence identity to SEQ ID NO: 4; or
(d) an ADH promoter comprising SEQ ID NO: 5 or a sequence with at least about 70% sequence identity to SEQ ID NO: 5.

13. The expression vector according to claim 8, wherein the polynucleotide encodes at least one LDH enzyme comprising SEQ ID NO: 6.

14. The expression vector according to claim 8, wherein the terminator is cytochrome-c oxidase ("CYC1").

15. The expression vector according to claim 14, wherein the CYC1 terminator comprises SEQ ID NO. 10 or a sequence with at least about 70% sequence identity to SEQ ID NO 10.

16. A method of producing a lactic acid, comprising:
   culturing the modified microorganism of claim 1 in a glucose-containing medium such that the modified microorganism produces lactic acid; and
   recovering the lactic acid from the medium.

17. The method of claim 16, wherein the medium has a pH of about 1.5 to about 4.5 during at least a portion of the culturing process.

18. The method of claim 17, wherein the medium has a pH of about 3.5 to about 3.6 at the start of the culturing process, and wherein the pH decreases during the culturing process.

19. The method of claim 16, further comprising producing lactide from the recovered lactic acid.

20. The method of claim 16, further comprising polymerizing the lactide to prepare a polylactide polymer.

21. A modified microorganism for production of lactic acid that expresses at least one heterologous lactate dehydrogenase ("LDH") enzyme of *Pelodiscus sinensis japonicas*.

22. An expression vector for constructing a modified microorganism of claim 1, comprising:
   a replication origin;
   a promoter;
   a polynucleotide encoding at least one LDH enzyme wherein the LDH enzyme is of *Pelodiscus sinensis japonicas;*
   and a terminator.

* * * * *

UNITED STATES PATENT AND TRADEMARK OFFICE
CERTIFICATE OF CORRECTION

PATENT NO. : 9,150,835 B2  
APPLICATION NO. : 13/531356  
DATED : October 6, 2015  
INVENTOR(S) : Soon Chun Chung et al.

Page 1 of 1

It is certified that error appears in the above-identified patent and that said Letters Patent is hereby corrected as shown below:

ON THE TITLE PAGE

Item (75) after "Inventors", the name of Inventor "Dae Huck Kweon" should read:

--Dae Hyuk Kweon--

Item (30) after "Foreign Application Priority Data" should recite the following additional priority application information:

--Dec. 21, 2011…(KR)……….10-2011-0139520--

Signed and Sealed this  
Fifteenth Day of March, 2016

Michelle K. Lee  
*Director of the United States Patent and Trademark Office*

SEQUENCE LISTING

```
<160> NUMBER OF SEQ ID NOS: 10

<210> SEQ ID NO 1
<211> LENGTH: 1267
<212> TYPE: DNA
<213> ORGANISM: K. marxianus

<400> SEQUENCE: 1
gagctccttt catttctgat aaaagtaaga ttactccatt tatcttttca ccaacatatt      60
catagttgaa agttatcctt ctaagtacgt atacaatatt aattaaacgt aaaaacaaaa     120
ctgactgtaa aaatgtgtaa aaaaaaaata tcaaattcat agcagtttca aggaatgaaa     180
actattatga tctggtcacg tgtatataaa ttattaattt taaacccata taatttatta     240 ttttttatt ctaaagttta aagtaatttt agtagtattt tatattttga ataaatatac     300
tttaaatttt tatttttata ttttattact tttaaaaata atgtttttat ttaaaacaaa     360
attataagtt aaaaagttgt tccgaaagta aaatatattt tatagttttt acaaaaataa     420 attatttta acgtatttt tttaattata tttttgtatg tgattatatc cacaggtatt     480
atgctgaatt tagctgtttc agtttaccag tgtgatagta tgattttttt tgcctctcaa     540
aagctatttt tttagaagct tcgtcttaga aataggtggt gtataaattg cggttgactt     600
ttaactatat atcattttcg atttatttat tacatagaga ggtgctttta attttttaat     660 tttattttc aataatttta aaagtgggta cttttaaatt ggaacaaagt gaaaaatatc     720
tgttatacgt gcaactgaat tttactgacc ttaaaggact atctcaatcc tggttcagaa     780
atccttgaaa tgattgatat gttggtggat tttctctgat tttcaaacaa gaggtatttt     840
atttcatatt tattatattt tttacattta ttttatattt ttttattgtt tggaagggaa     900
agcgacaatc aaattcaaaa tatattaatt aaactgtaat acttaataag agacaaataa     960
cagccaagaa tcaaatactg ggtttttaat caaaagatct ctctacatgc acccaaattc    1020
attatttaaa tttactatac tacagacaga atatacgaac ccagattaag tagtcagacg    1080
cttttccgct ttattgagta tatagcctta catattttct gcccataatt tctggattta    1140
aaataaacaa aaatggttac tttgtagtta tgaaaaaagg cttttccaaa atgcgaaata    1200
cgtgttattt aaggttaatc aacaaaacgc atatccatat gggtagttgg acaaaacttc    1260
aatcgat                                                              1267
```

<210> SEQ ID NO 2
<211> LENGTH: 289
<212> TYPE: DNA
<213> ORGANISM: Saccharomyces cerevisiae

<400> SEQUENCE: 2

```
atttggcgag cgttggttgg tggatcaagc ccacgcgtag gcaatcctcg agcagatccg      60
ccaggcgtgt atatatagcg tggatggcca ggcaacttta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289
```

<210> SEQ ID NO 3
<211> LENGTH: 401
<212> TYPE: DNA
<213> ORGANISM: Saccharomyces cerevisiae

<400> SEQUENCE: 3

```
atagcttcaa aatgtttcta ctcctttttt actcttccag attttctcgg actccgcgca      60
tcgccgtacc acttcaaaac acccaagcac agcatactaa atttcccctc tttcttcctc     120
tagggtgtcg ttaattaccc gtactaaagg tttggaaaag aaaaaagaga ccgcctcgtt     180
tcttttttctt cgtcgaaaaa ggcaataaaa attttttatca cgtttctttt tcttgaaaat     240
tttttttttg attttttttct ctttcgatga cctcccattg atatttaagt taataaacgg     300
tcttcaattt ctcaagtttc agtttcattt ttcttgttct attacaactt tttttacttc     360
ttgctcatta gaaagaaagc atagcaatct aatctaagtt t                         401
```

<210> SEQ ID NO 4
<211> LENGTH: 655
<212> TYPE: DNA
<213> ORGANISM: Saccharomyces cerevisiae

<400> SEQUENCE: 4

```
agtttatcat tatcaatact cgccatttca aagaatacgt aaataattaa tagtagtgat      60
tttcctaact ttatttagtc aaaaaattag cctttaatt ctgctgtaac ccgtacatgc      120
ccaaaatagg gggcgggtta cacagaatat ataacatcgt aggtgtctgg gtgaacagtt     180
tattcctggc atccactaaa tataatggag cccgcttttt aagctggcat ccagaaaaaa     240
aaagaatccc agcaccaaaa tattgttttc ttcaccaacc atcagttcat aggtccattc     300
tcttagcgca actacagaga acaggggcac aaacaggcaa aaacgggca caacctcaat      360
ggagtgatgc aacctgcctg gagtaaatga tgacacaagg caattgaccc acgcatgtat     420
ctatctcatt ttcttacacc ttctattacc ttctgctctc tctgatttgg aaaaagctga     480
aaaaaaaggt tgaaaccagt tccctgaaat tattccccta cttgactaat aagtatataa     540
agacggtagg tattgattgt aattctgtaa atctatttct taaacttctt aaattctact     600
tttatagtta gtcttttttt tagttttaaa acaccagaac ttagtttcga cggat          655
```

<210> SEQ ID NO 5
<211> LENGTH: 1468
<212> TYPE: DNA
<213> ORGANISM: Saccharomyces cerevisiae

<400> SEQUENCE: 5

```
gccgggatcg aagaaatgat ggtaaatgaa ataggaaatc aaggagcatg aaggcaaaag      60
acaaatataa gggtcgaacg aaaaataaag tgaaaagtgt tgatatgatg tatttggctt     120
tgcggcgccg aaaaaacgag tttacgcaat tgcacaatca tgctgactct gtggcggacc     180
cgcgctcttg ccggcccggc gataacgctg ggcgtgaggc tgtgcccggc ggagtttttt     240
gcgcctgcat tttccaaggt ttaccctgcg ctaaggggcg agattggaga agcaataaga     300
atgccggttg gggttgcgat gatgacgacc acgacaactg tgtcattat ttaagttgcc      360
gaaagaacct gagtgcattt gcaacatgag tatactagaa gaatgagcca agacttgcga     420
gacgcgagtt tgccggtggt gcgaacaata gagcgaccat gaccttgaag gtgagacgcg     480
cataaccgct agagtacttt gaagaggaaa cagcaatagg gttgctacca gtataaatag     540
acaggtacat acaacactgg aaatggttgt ctgtttgagt acgctttcaa ttcatttggg     600
tgtgcacttt attatgttac aatatggaag gaactttac acttctccta tgcacatata      660
ttaattaaag tccaatgcta gtagagaagg ggggtaacac ccctccgcgc tcttttccga    720
ttttttttcta aaccgtggaa tatttcggat atccttttgt tgtttccggg tgtacaatat   780
ggacttcctc ttttctggca accaaaccca tacatcggga ttcctataat accttcgttg    840
gtctccctaa catgtaggtg gcggagggga gatatacaat agaacagata ccagacaaga   900
cataatgggc taaacaagac tacaccaatt acactgcctc attgatggtg gtacataacg   960
aactaatact gtagccctag acttgatagc catcatcata tcgaagtttc actacccttt  1020
ttccatttgc catctattga agtaataata ggcgcatgca acttcttttc ttttttttc    1080
ttttctctct cccccgttgt tgtctcacca tatccgcaat gacaaaaaaa tgatggaaga  1140
cactaaagga aaaattaac gacaaagaca gcaccaacag atgtcgttgt tccagagctg   1200
atgaggggta tctcgaagca cacgaaactt tttccttcct tcattcacgc acactactct  1260
ctaatgagca acggtatacg gccttccttc cagttacttg aatttgaaat aaaaaaagt    1320
ttgctgtctt gctatcaagt ataaatagac ctgcaattat taatcttttg tttcctcgtc  1380
attgttctcg ttcccttct tccttgtttc ttttttctgca caatatttca agctatacca  1440
agcatacaat caactccaag ctggccgc                                      1468
```

<210> SEQ ID NO 6
<211> LENGTH: 332
<212> TYPE: PRT
<213> ORGANISM: Pelodiscus sinensis japonicus

<400> SEQUENCE: 6

```
Met Ser Val Lys Glu Leu Leu Ile Gln Asn Val His Lys Glu Glu His
1               5                   10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110
```

```
Asn Val Asn Ile Phe Lys Phe Ile Ile Pro Asn Val Lys Tyr Ser
            115                 120                 125

Pro Asp Cys Met Leu Leu Val Val Ser Asn Pro Val Asp Ile Leu Thr
        130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
                180                 185                 190

His Gly Asp Ser Ser Val Pro Val Trp Ser Gly Val Asn Val Ala Gly
                195                 200                 205

Val Ser Leu Lys Ala Leu Tyr Pro Asp Leu Gly Thr Asp Ala Asp Lys
        210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
        260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
        290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 7
<211> LENGTH: 332
<212> TYPE: PRT
<213> ORGANISM: Ornithorhynchus anatinus

<400> SEQUENCE: 7

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Asn Cys Lys Leu Leu Val Val Ser Asn Pro Val Asp Ile Leu Thr
        130                 135                 140

Tyr Val Ala Trp Lys Ile Ser Gly Phe Pro Lys Asn Arg Val Ile Gly
145                 150                 155                 160
```

```
Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330
```

<210> SEQ ID NO 8
<211> LENGTH: 332
<212> TYPE: PRT
<213> ORGANISM: Tursiops truncatus
<400> SEQUENCE: 8

```
Met Ala Thr Val Lys Asp Gln Leu Ile Gln Asn Leu Leu Lys Glu Glu
1               5                   10                  15

His Val Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
```

```
                195                 200                 205
Val Ser Leu Lys Asn Leu His Pro Glu Leu Gly Thr Asp Ala Asp Lys
210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
                260                 265                 270

Ile Ser Thr Met Ile Lys Gly Leu Tyr Gly Ile Lys Glu Asp Val Phe
                275                 280                 285

Leu Ser Val Pro Cys Ile Leu Gly Gln Asn Gly Ile Ser Asp Val Val
                290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 9
<211> LENGTH: 332
<212> TYPE: PRT
<213> ORGANISM: Rattus norvegicus

<400> SEQUENCE: 9

```
Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
                35                  40                  45

Ala Leu Val Asp Val Ile Glu Asp Lys Leu Lys Gly Glu Met Met Asp
            50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
                100                 105                 110

Asn Val Asn Ile Phe Lys Phe Ile Ile Pro Asn Val Val Lys Tyr Ser
                115                 120                 125

Pro Gln Cys Lys Leu Leu Ile Val Ser Asn Pro Val Asp Ile Leu Thr
                130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
                180                 185                 190

His Gly Asp Ser Ser Val Pro Val Trp Ser Gly Val Asn Val Ala Gly
                195                 200                 205

Val Ser Leu Lys Ser Leu Asn Pro Gln Leu Gly Thr Asp Ala Asp Lys
210                 215                 220

Glu Gln Trp Lys Asp Val His Lys Gln Val Val Asp Ser Ala Tyr Glu
225                 230                 235                 240
```

```
Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
            290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 10
<211> LENGTH: 252
<212> TYPE: DNA
<213> ORGANISM: Saccharomyces cerevisiae

<400> SEQUENCE: 10
tcatgtaatt agttatgtca cgcttacatt cacgccctcc ccccacatcc gctctaaccg      60
aaaaggaagg agttagacaa cctgaagtct aggtccctat ttattttttt atagttatgt     120
tagtattaag aacgttattt atatttcaaa tttttctttt ttttctgtac agacgcgtgt     180
acgcatgtaa cattatactg aaaaccttgc ttgagaaggt tttgggacgc tcgaaggctt     240
taatttgcgg cc                                                         252
```